(12) United States Patent
Ostrovsky et al.

(10) Patent No.: US 7,806,893 B2
(45) Date of Patent: Oct. 5, 2010

(54) APPARATUS AND METHOD FOR MAKING A SPHERICAL LESION

(75) Inventors: Isaac Ostrovsky, Wellesley, MA (US); Ty Fairneny, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 355 days.

(21) Appl. No.: 11/114,829

(22) Filed: Apr. 26, 2005

(65) Prior Publication Data

US 2006/0241738 A1    Oct. 26, 2006

(51) Int. Cl.
*A61B 18/14*    (2006.01)
(52) U.S. Cl. .......................................... 606/41
(58) Field of Classification Search ................... 606/41, 606/48, 50
See application file for complete search history.

(56) References Cited

U.S. PATENT DOCUMENTS

| | | | |
|---|---|---|---|
| 6,231,570 B1 * | 5/2001 | Tu et al. ...................... | 606/41 |
| 6,544,262 B2 * | 4/2003 | Fleischman ................... | 606/41 |
| 6,575,967 B1 | 6/2003 | Leveen et al. | |
| 7,195,629 B2 * | 3/2007 | Behl et al. ..................... | 606/41 |
| 7,306,595 B2 * | 12/2007 | Ostrovsky et al. ............. | 606/41 |
| 7,416,549 B2 * | 8/2008 | Young et al. ................... | 606/41 |
| 7,520,877 B2 * | 4/2009 | Lee et al. ....................... | 606/42 |
| 7,524,318 B2 * | 4/2009 | Young et al. ................... | 606/41 |
| 2004/0230187 A1 | 11/2004 | Lee et al. | |
| 2005/0065509 A1 * | 3/2005 | Coldwell et al. .............. | 606/41 |
| 2005/0080409 A1 | 4/2005 | Young et al. | |

FOREIGN PATENT DOCUMENTS

DE    103 45 023 A1    4/2005

* cited by examiner

*Primary Examiner*—Lee S Cohen
(74) *Attorney, Agent, or Firm*—Fay Kaplun & Marcin, LLP

(57) ABSTRACT

An electrode assembly for a bi-polar ablation system comprises a first electrode array including a plurality of first tines, each of the first tines, when in a deployed configuration, extending substantially radially away from a center of the first array and including a substantially straight central portion in combination with a second electrode array including a plurality of second tines, each of the second tines, when in the deployed configuration, extending radially away from a center of the second array and including a substantially straight central portion substantially parallel to the central portion of a corresponding one of the first tines.

14 Claims, 6 Drawing Sheets

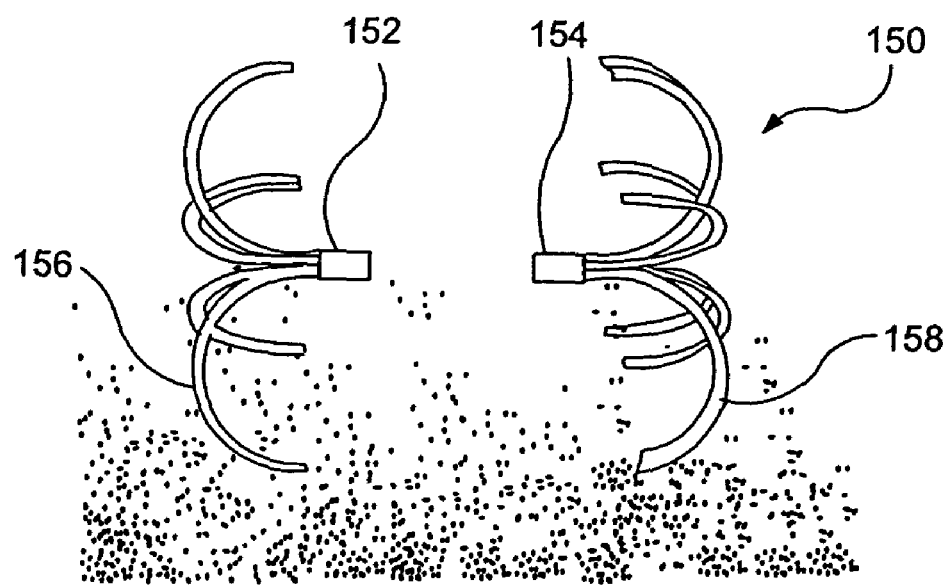
F I G. 2
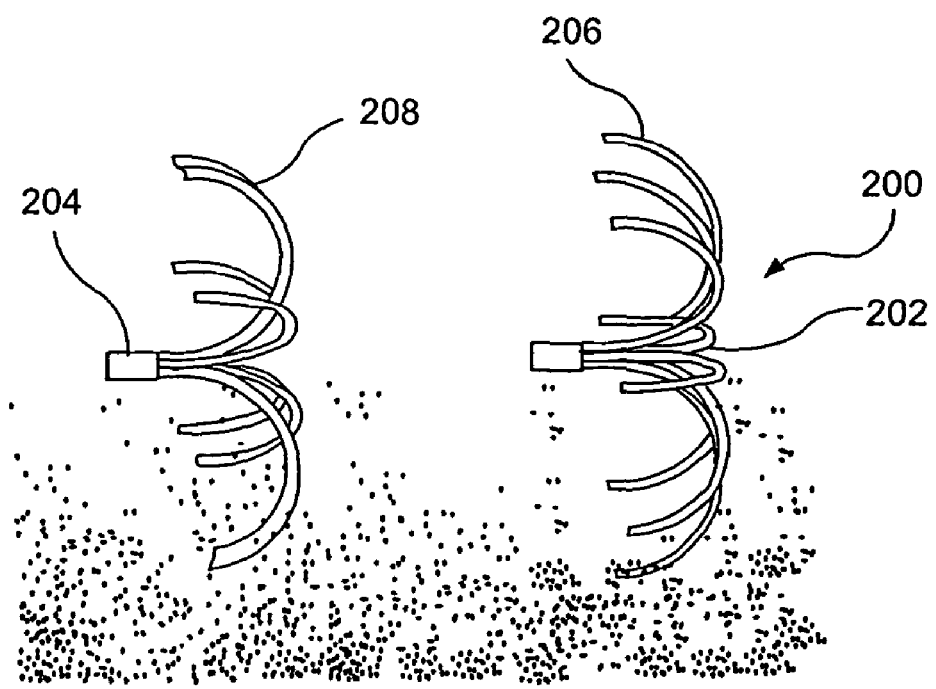
F I G. 3

APPARATUS AND METHOD FOR MAKING A SPHERICAL LESION

BACKGROUND

Fibroids, tumors and other tissue masses are often treated by ablation. In many cases, local ablation of the diseased tissue is carried out by inserting a therapeutic device into the tissue and carrying out therapeutic activity designed to destroy the diseased cells. For example, electrical energy (usually alternative current of radio frequency—RF) may be applied to the affected area by placing one or more electrodes into the affected tissue and discharging electric current therefrom to ablate the tissue. Alternatively, tissue may be ablated cryogenically, by applying heat or chemically by injecting fluids with appropriate properties to the target tissue.

When electrical energy is used, the size and shape of the region of tissue ablated depends, in part, on the configuration of the electrodes used for the procedure and on the strength of the charge applied. The electrical energy dissipates very rapidly with distance from the electrodes, it has been difficult to maintain desired levels of energy density within large volumes of tissue. Therefore, the ablation of larger target tissue masses has often necessitated repeated application of the ablation electrodes at multiple locations within each target tissue mass. This repetition increases the complexity, duration and cost of these procedures.

In addition, the shapes and sizes of lesions formed by existing RF ablation systems often do not reflect the shapes of the target tissue masses. For example, tumors are often generally spherical and some of them are quite large. The shapes of tissue masses ablated by conventional monopolar ablation systems are generally spherical, but the tissue masses affected are small, while conventional bipolar ablation methods produce bigger thermal mass, but ablate substantially cylindrical shapes. In both these cases, repeated applications and the ablation of substantial amounts of non-targeted tissue may be necessary to achieve a desired degree of ablation throughout an entire target tissue mass.

SUMMARY OF THE INVENTION

In one aspect, the present invention is directed to an electrode assembly for a bi-polar ablation system comprising a first electrode array including a plurality of first tines, each of the first tines, when in a deployed configuration, extending substantially radially away from a center of the first array and including a substantially straight central portion and a second electrode array including a plurality of second tines, each of the second tines, when in the deployed configuration, extending radially away from a center of the second array and including a substantially straight central portion substantially parallel to the central portion of a corresponding one of the first tines.

The present invention is further directed to a method for ablating tissue, comprising deploying a first electrode array at a first desired position relative to a target tissue mass to be ablated, the first array comprising a plurality of first tines, each of the deployed first tines including a substantially straight central portion and deploying a second electrode array at a second desired position relative to the target tissue mass, the second array comprising a plurality of second tines, each of the deployed second tines including a substantially straight central portion, the central portions of the first and second tines being oriented and positioned so that a distance between corresponding pairs of the first and second tines is substantially constant along the lengths thereof, the second desired position being separated from the first desired position by a distance between one quarter and one half of a deployed diameter of the first and second arrays in combination with applying one of RF and electrical energy to the first and second arrays to ablate a first portion of the target tissue mass, repositioning at least one of the first and second arrays to a third desired position relative to the target tissue mass to increase a distance between the first and second arrays and applying one of RF and electrical energy the first and second arrays to ablate a second portion of the target tissue mass.

BRIEF DESCRIPTION OF DRAWINGS

FIG. 2 shows a diagram of a first type of conventional bipolar tissue ablation system;

FIG. 3 shows a diagram of a second type of conventional bipolar tissue ablation system;

DETAILED DESCRIPTION

Figure 1:
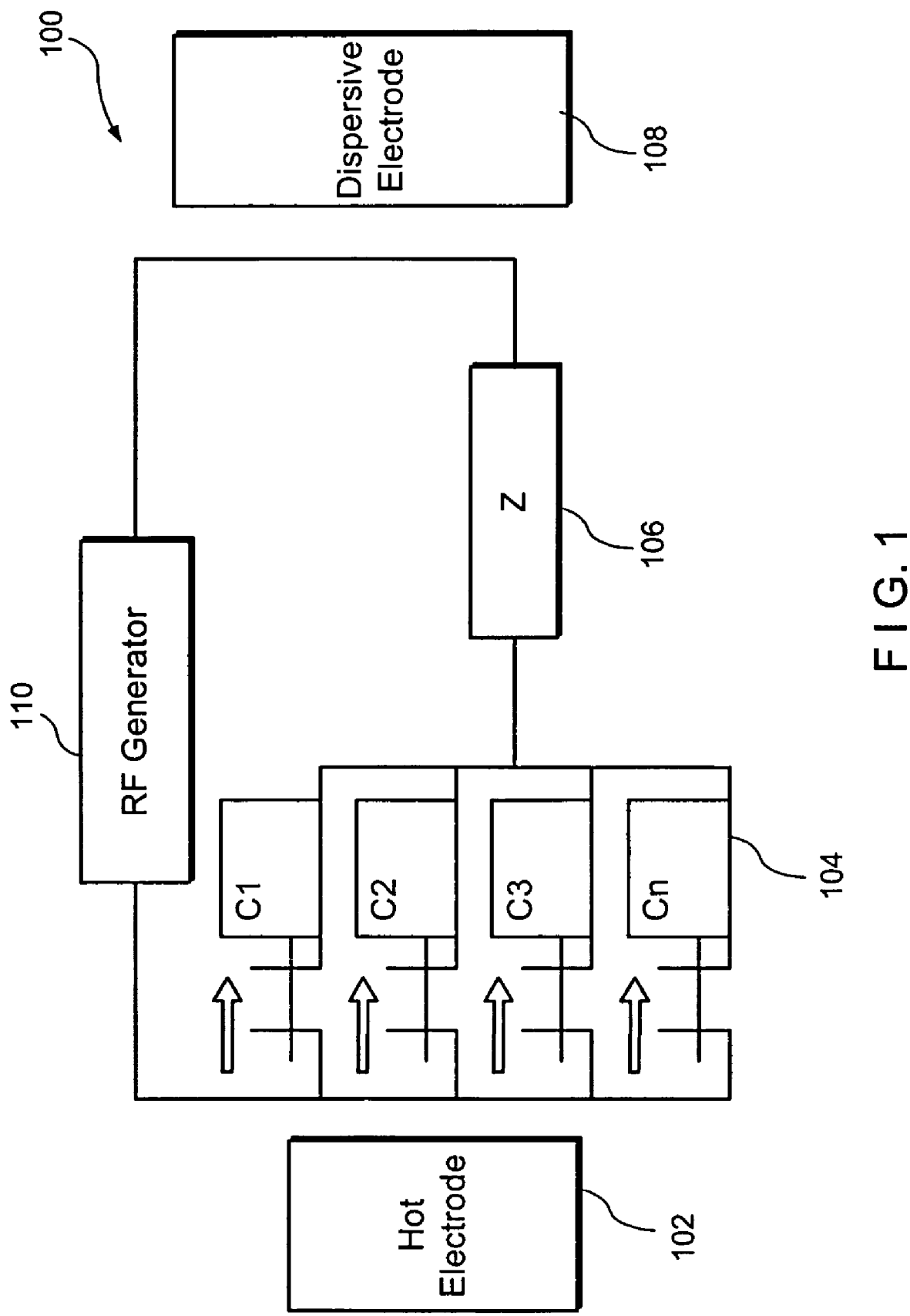
FIG. 1 shows an electrical diagram of a monopolar tissue ablation system.

The present invention may be further understood with reference to the following description and the appended drawings, wherein like elements are referred to with the same reference numerals. Embodiments of the present invention relate to methods and systems for ablating targeted tissues within a patient's body. In particular, the embodiments are related to the ablation of target tissues using electric energy of radio frequency.

During RF or electric discharge ablation, one or more electrodes are placed in contact with or adjacent to a target tissue mass and electric or RF energy is applied to the electrodes to necrose the tissue of the target tissue mass. In one type of procedure, electrodes are placed within the target tissue mass, for example, by puncturing an outer surface of the target tissue and inserting the electrodes therein.

RF ablation systems typically fall into one of two broad categories: monopolar and bipolar. Monopolar systems include only one active electrode which is inserted into the body in, or adjacent to, the target tissue mass. A dispersive electrode, or other similar device, is placed on the skin of the patient to provide a return path for the electric current. A "loop" is thus formed, which includes the active electrode, the target tissue and the dispersive electrode. Bipolar electrode systems, on the other hand, include two active electrodes of alternating polarity both of which are inserted in close proximity to one another adjacent to the target tissue mass. Bipolar systems tend to be more efficient since both active electrodes produce heat near the target tissue mass allowing delivered energy to be better focused on the target tissue mass. Shaping and positioning the electrodes of a bipolar system also allows the shape of the region tissue ablated to be maximized and more closely controlled.

As mentioned above, the size of the lesions which can be produced by monopolar systems is limited as only one implanted electrode is used. As a result, even using multi-tine electrodes such as the LEVEEN® Needle Electrode manufactured by Boston Scientific Oncology Division, larger target tissue masses may require multiple applications before they are fully treated. Half the energy transmitted in monopolar systems is dissipated at the dispersive electrode without producing heat. In addition, as the distance between the electrodes of a monopolar system is usually substantial, the path along which current will flow to the dispersive electrode cannot be completely predicted. Thus, energy may be applied to non-targeted tissue possibly including tissue to which it is desired not to apply energy.

As described above, the generally cylindrical lesion shapes obtained using conventional bipolar systems are not well suited to treat many tumors, which tend to be substantially spherical. Additional procedures are carried out at times to modify the shape of the resulting lesion. For example, water cooling or saline injections may be made in and around the target tissue mass, to inhibit or enhance the transfer of heat to portions of tissue selected to generate a lesion of a desired shape. These procedures increase the complexity, time and cost of the RF/electrical ablation treatment, and may not always provide acceptable results.

Embodiments of the present invention allow the formation of large spherical lesions without performing additional procedures or employing additional devices which complicate the procedure. Embodiments of the present invention may thus be used to treat large, substantially spherical tumors in one setting, while minimizing injury to surrounding non-targeted tissues, and without requiring insertion of the electrodes in different regions of the target tissue mass.

To understand the present invention, it is useful to describe the mechanisms by which RF energy creates lesions. Initially, the lesion is generated as tissue absorbs RF energy with the energy (Q) absorbed per unit area of the tissue in a direction perpendicular to a direction of current flow being described by the equation:

$$Q = i^2 Z \Delta t$$

where i is an RF current density, Z is a resistivity of the tissue and $\Delta t$ is the time during which energy is applied. As the lesion grows, subsequent heating of the tissue is carried out by conduction of heat from the initial, central zone of the lesion. The heat flow (F) in this condition is described by the equation:

$$F = -kA\Delta T^o \Delta t / R$$

where k is a thermal conductivity coefficient of the tissue, A is a heat zone surface area, R is a distance from the heat source, $\Delta T^o$ is a temperature differential and $\Delta t$ is the time elapsed.

Theoretically, a lesion will continue to grow so long as an amount of energy deposited exceeds an outflow of heat (Q>F) as the component A of the second equation would grow to balance the energy deposited. If the tissue were not subject to any external cooling processes, the lesion would continue to grow for as long as a temperature differential was maintained (i.e., for as long as electrical energy were supplied to the tissue). However, if external cooling is applied to the system, the rate of deposition of electrical energy into the tissue would need to continually increase to indefinitely continue increasing the size of the lesion. Over time, the power required would increase significantly as the increase in the surface area of the ablated region would increase and, consequently, the heat flow would increase as well. When the power of an electrical energy source remains constant, a thermal equilibrium condition is reached as the lesion reaches an equilibrium size where the energy dispersed over the surface area of the lesion is no longer sufficient to ablate the contiguous tissue. Thus, lesion grows no further.

There is also a practical limit to the amount of electrical energy which may be applied to target tissue via an electrode. When the temperature at the surface of the electrode reaches a value at which vapor starts to form, a maximum energy transfer rate for that size of electrode has been reached. The vapor forms an insulating layer around the tines of the electrode and prevents additional current from flowing from the electrode into the tissue. To deposit more energy into the tissue, it is necessary to increase the current deposition surface area (e.g., by using additional or larger electrodes) to apply more energy to the tissue while remaining below the vapor formation temperature.

During monopolar RF ablation, the current density (i) on the surface of an electrode is a function of the surface area of the electrode, and is given by the equation: $i = I/A_{el}$. Thus, larger surface area electrodes inject more current or power into the tissue, while maintaining a lower electrode surface current density and, consequently, a lower electrode surface temperature. Thus, many electrode designs have maximized the surface area of the electrodes positioned in a given volume of target tissue. As the dispersive electrode of a monopolar system is much larger and further away from the electrode placed in contact with the target tissue, current from each element of the active electrode spreads in all directions, forming an equipotential surface that, depending on the properties of the surrounding tissue, may approximate a sphere.

A monopolar RF ablation system may be modeled by approximating it with an equivalent electrical circuit as shown in FIG. 1. In this representation, the RF generator 110 has a hot, or active electrode 102 which is placed in contact with or adjacent to a target tissue mass. C1, C2, C3 . . . Cn represent electrical contact points 104 formed at small areas of an interface between tissue and the surface of the electrode 102. The elements of the active electrode 102 all have substantially the same electrical resistance Z with respect to the dispersive electrode 108, due to the long path between these electrodes, which translates into high resistance. The difference in the paths between the dispersive electrode 108 and the various contact points 104 is insubstantial (i.e., within the dimensions of the active electrode). Thus the difference in resistance along these paths is not significant and may be ignored. As a result, the current density over the various contact points 104 is substantially constant. During application of the RF energy, the surrounding tissue heats up and its impedance drops, increasing the current density. Since all of the contact points 104 along the electrode 102 are in substantially the same electrical situation, this process goes on uniformly across the surface of the electrode 102. At some point, however, vapor begins to form at the interface between the electrode 102 and the tissue creating an insulating layer between the electrode 102 and the tissue. In the schematic diagram of FIG. 1, this is shown by opening one or more of the contact points 104.

The current density (i) through a spherical portion of tissue is given by:

$$i = I/A = I/4\pi R^2$$

Thus, current density decreases in proportion to the square of the distance from the probe. The RF power (P) absorbed by the tissue decreases in proportion to the distance from the electrode raised to the fourth power, as given by the equation:

$$P = i^2 Z = I^2 Z / 16 R^4$$

In these conditions, the RF power heats only a small portion of tissue which is typically located within a few millimeters of the surface of the electrode 102.

As described above, bipolar RF ablation methods are generally more efficient than monopolar methods. Currently, there are two principal bi-polar electrode designs in use. FIG. 2 shows one type of RF ablation system 150, in which tines 156, 158 of the two arrays 152, 154 are shaped like opposing open umbrellas to encompass a generally spherical target tissue volume. FIG. 3 shows a second common bipolar system 200, in which the arrays 202, 204 are oriented substantially in the same direction. In the latter configuration, the insertion and deployment of the tines 206, 208 may be easier, especially if they are inserted in the same direction from a single incision.

Figure 7:
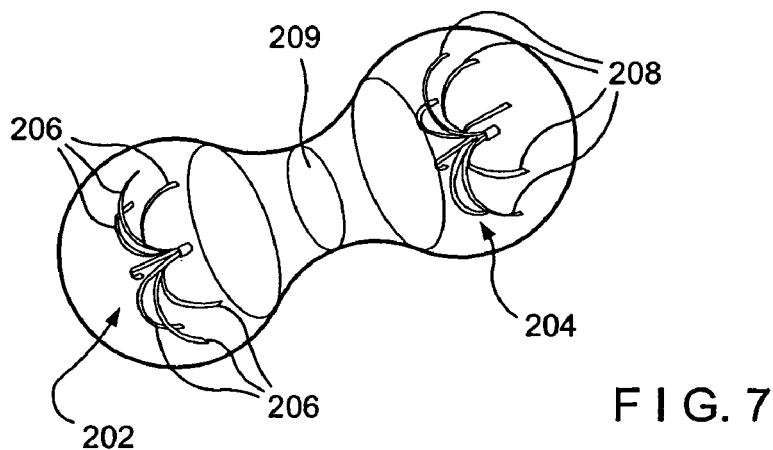
FIG. 7 is a diagram showing heat generation zones for the bipolar system of FIG. 3 with electrode arrays thereof in a first position.

For various reasons, e.g., to make a larger lesion, the arrays of tines may be placed further apart. As shown in FIG. 7, under these conditions, each of the arrays of electrodes acts substantially as a separate monopolar electrode forming lesions 207 therearound. Depending on the spacing of the arrays 202, 204, it may be very difficult to combine such lesions into a larger, unitary lesion beyond a small central connection area 209.

Figure 8:
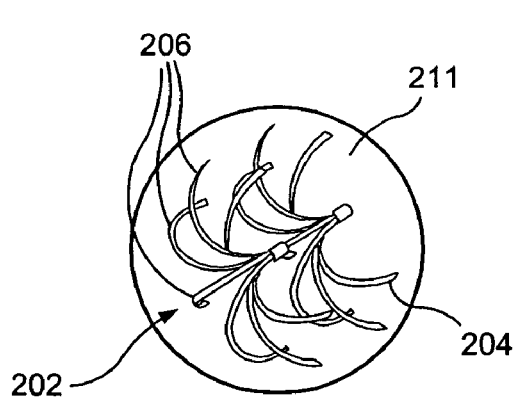
FIG. 8 is a diagram showing heat generation zones for the bipolar system of FIG. 3 with the electrode arrays thereof in a second position.
Figure 9:
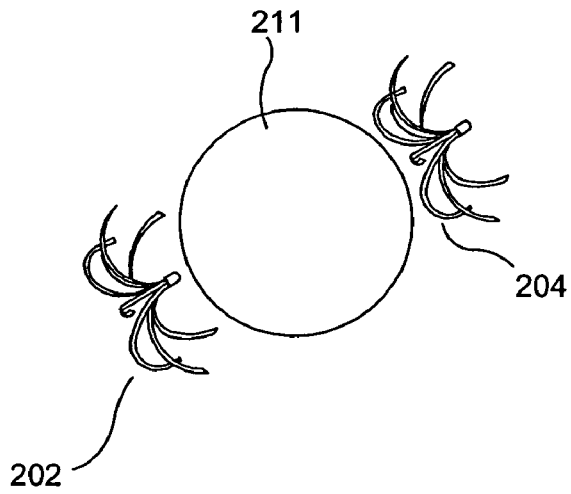
FIG. 9 is a diagram showing the bipolar system of FIG. 3 in the first position after an initial ablation performed with the arrays in the first position.
Figure 10:
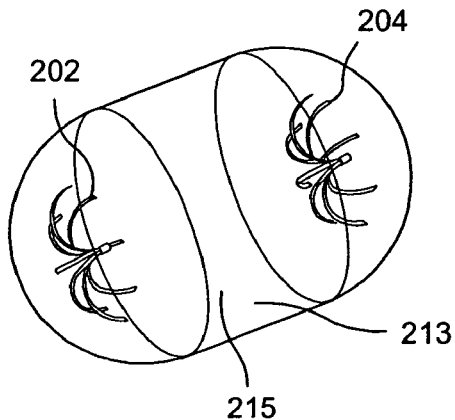
FIG. 10 is a diagram showing the bipolar system of FIG. 3 after ablation in the second position following an initial ablation performed with the arrays in the first position.

FIGS. 8-10 show a multi-stage ablation method. As shown in FIG. 8, in an initial stage, the electrode arrays 202, 204 are placed closer to one another and energy is applied to form an initial lesion of limited size which also represents a volume 211 of higher impedance. Then as a second step (FIG. 9), the electrode arrays 202, 204 are spread further apart (e.g., a distal electrode is pushed forward and a proximal electrode is pulled back) with the initial lesion/high impedance volume 211 centered therebetween. When energy is applied in this position, current flows around the high impedance volume 211 affecting more tissue in a transverse direction to generate a single lesion 213 incorporating the initial lesion/high impedance volume 211 which, while closer to spherical than the shape of the combined lesions 207 of FIG. 7, includes a central portion 215 which is more cylindrical than spherical. According to this embodiment, as the axial dimension of the arrangement formed by the two active electrode arrays 202, 204 is larger than its radial extent, to obtain a more spherical lesion, the active electrode arrays are preferably positioned close to one another (e.g., separated by a distance less than a radial extent of the arrays). Thus, the initial lesion will extend further in the radial dimension than axially. Subsequent lesions, will increase the axial extent of the lesion more quickly than the radial extent as the electrode arrays 202, 204 are separated further from one another making the lesion more spherical.

Figure 4:
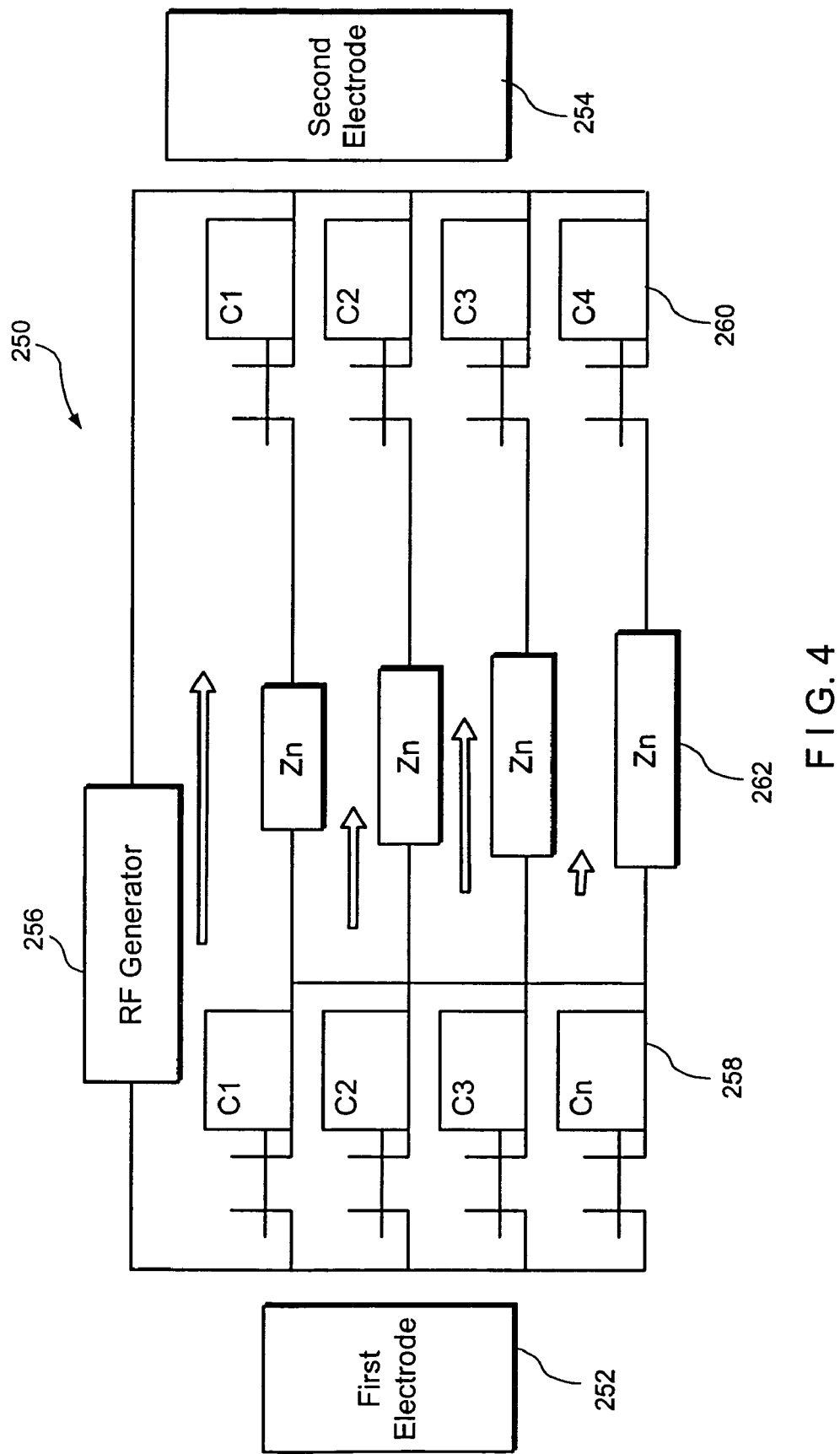
FIG. 4 shows an equivalent electrical diagram of a bipolar tissue ablation system.

With the current, curved, umbrella shaped electrode arrays 202, 204, it may be difficult to place the arrays close enough to one another to produce a spherical lesion due to the risk of short circuiting should the arrays touch one another. Furthermore, the curved shape of these electrode arrays 202, 204 may create a situation where some elements 206, 208 of the active electrode arrays 202, 204, respectively, may be close to one another while other elements 206, 208 of the arrays 202, 204, respectively, remain further apart. As shown in FIG. 4, an electrical system substantially equivalent to such a bipolar system 250 comprises an RF generator 256 operatively connected to electrode arrays 252, 254 via conventional conductors and connectors. The electrode arrays 252, 254 may be, for example, umbrella shaped arrays of tines as described above. The contacts C1, C2, C3, Cn represent interface contacts between the surfaces of the electrode arrays 252, 254 and the tissue 262. The different resistances Z1, Z2, Z3, Zn, connected in parallel, represent the different path lengths between the elements of the electrodes 252, 254. Since the resistances are all unequal, the system produces different current densities $i1, i2, i3 \ldots i_n$ through the portions of tissue 262. As a result, the temperature distribution along the elements of the electrode arrays 252, 254 is quite uneven with higher temperatures at the surfaces of those elements of the electrode arrays 252, 254 close to one another creating a higher impedance drop in the these regions which, in turn, results in an even higher current density in these regions. A snowball effect thus can take place with high temperatures leading to lower impedances which lead to even higher temperatures.

The snowball effect typically ends quickly when the temperature of the closest corresponding elements of the opposing arrays 252, 254 becomes sufficiently high to cause the formation of vapor. Vapor around the electrodes effectively opens a contact in the equivalent circuit, for example at C1 in the diagram, and shuts off the heating from that element. This in turn increases the overall impedance between the electrode arrays 252, 254 and reduces the current and power which may be deposited into the tissue by the electrode arrays 252, 254. Ultimately, this mechanism places a limit to the size of the lesion which can be obtained using conventional electrode arrays 252, 254 of the type described above.

As described, the shape and volume of the area affected by the current distribution between the electrodes 252, 254 when in close proximity to one another depends on the distance between the elements of the electrodes 252, 254. When paired elements are further from one another, each one of the pair acts like a point source, distributing current in all directions with a current density distribution that is substantially inversely proportional to the square of the distance to the element. When the electrode arrays 252, 254 are close to one another, current is conducted more directly between paired elements approximating a straight line along an axis between the elements. The current density distribution between the elements in this case is substantially inversely proportional to the first power distance to the elements. In this case, the axis is a line substantially perpendicular to planes in which tips of the electrodes 252, 254 reside.

Figure 5A:
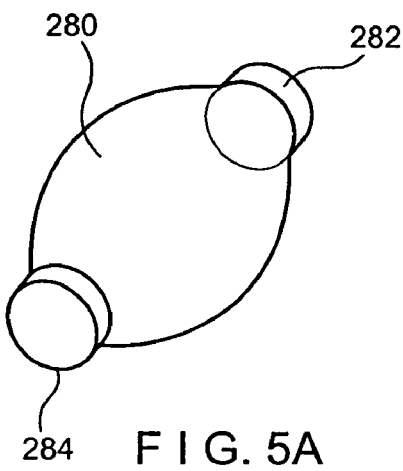
FIG. 5A is a diagram showing the energy distribution between elements of the electrodes of an RF ablation system in a first position.
Figure 5B:
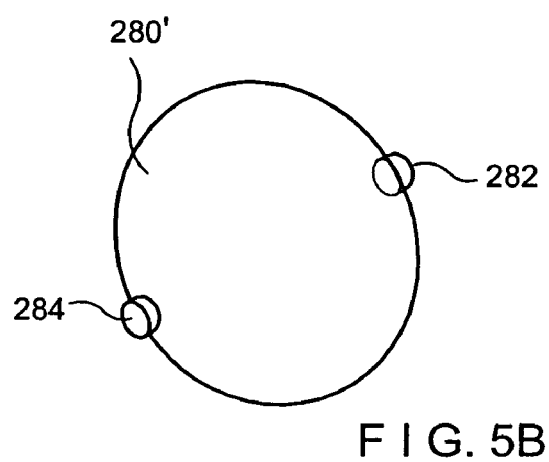
FIG. 5B is a diagram showing the energy distribution between elements of the electrodes of an RF ablation system in a second position.

FIG. 5 shows an example of an energy volume 280 between electrode elements 282, 284. As can be seen, for pairs of elements that are close to one another as in FIG. 5A, the current density and energy applied to target tissue are significantly different than the current density and energy applied between pairs of elements that are further from one another as represented by the energy volume 280' of FIG. 5B. The energy applied to tissue along a current path between elements that are close to one another is inversely proportional to the square of the distance as opposed to being proportional to the fourth power of the distance for elements further from one another. Thus, when curved, umbrella-shaped electrode arrays are close to one another, the lesions formed are larger axially than radially and the lesion formation time is shorter because of the snowball effect, limiting the size of the lesions which can be created.

Figure 6:
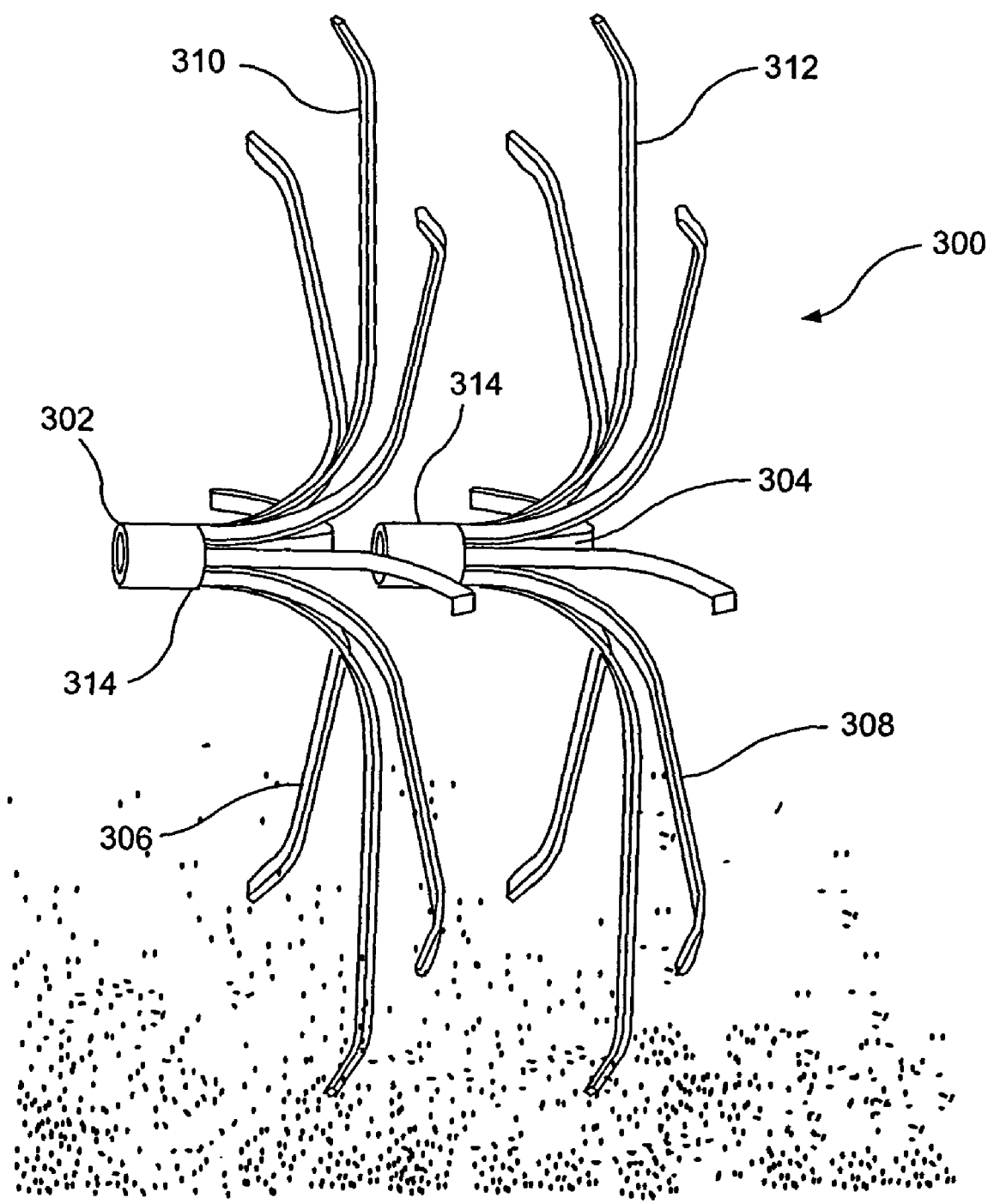
FIG. 6 is a diagram showing an exemplary embodiment of a bipolar RF ablation system according to the invention.

FIG. 6 shows an exemplary embodiment of a bipolar RF ablation system 300 according to the present invention comprising first and second electrode arrays 302, 304, respectively. The geometry of the tines 306, 308 of the first and second arrays 302, 304, respectively, is such that it is possible to bring the two arrays in close proximity after they have been deployed within or adjacent to the target tissue mass. For example, the two arrays 302, 304 may be moved toward one another to a distance of less than half the diameter of the array, while ensuring that none of the elements of the first array 302 contact any of the elements of second array 304 avoiding the problem of short circuit.

Another feature of the exemplary embodiment of the bipolar array according to the present invention is that the tines of each array are shaped to promote a more uniform distribution of current within the target tissue. For example, the tines 306 and 308 comprise, respectively, linear portions 310, 312 which face each other when the arrays of tines 302, 304 are deployed. The linear portions 310, 312 result in a substantially uniform distance between corresponding ones of tines 306, 308, at least along the lengths of the linear portions 310, 312 which may, for example, comprise the majority of the lengths of the tines 306, 308. The substantially uniform distance between the tines 306, 308 helps to maintain a more uniform current density along the surfaces of the electrode arrays 302, 304, and generates a more uniform application of energy to the surrounding tissue.

The close and substantially uniform distance between the tines 306, 308 allows the generation of a substantially uniform current density distribution between the arrays 302, 304 as shown in FIG. 5A. Thus, energy distribution along the tines 306, 308 and along the axis is substantially uniform preventing the snowball effect and resulting in a larger, more homogeneous lesion. This may be especially valuable when using a multi-step ablation process. As would be understood by those skilled in the art, employing the system 300, careful selection of the initial and subsequent distances between the electrodes 302, 304 will allow the creation of large, substantially cylindrical lesions. In order to achieve the most uniform energy distribution, when deployed, the linear portions 310, 312 are preferably arranged in first and second planes substantially perpendicular to the central axis. However, for other reasons associated, for example, with deployment and storage during insertion, the tines may deploy so that the linear portions 310, 312 are located along portions of first and second cones with an angle of the cones being between 60 and 90 degrees.

The exemplary bipolar system 300 according to the invention is preferably inserted to the target tissue mass in a folded, insertion configuration, as is common for RF ablation electrodes. Once the electrodes are in a desired position relative to the target tissue mass, the arrays of tines 302, 304 are deployed using conventional mechanisms as would be understood by those skilled in the art to an extended, operative configuration which, in the exemplary embodiment, comprises a substantially circular, umbrella-like shape. A translation mechanism is preferably provided to move the arrays of tines 302, 304, for example, along a longitudinal axis of the system 300 to deploy the arrays 302, 304. Specifically, core portions 314 of the arrays 302, 304 are preferably connected to this mechanism to extend the tines 306, 308 from and retract the tines 306, 308 into a cannula or sheath as would be understood by those skilled in the art. The mechanism may also, provide for translation of the arrays of tines 302, 304 along the longitudinal axis relative to one another, to vary the distance therebetween.

Figure 11:
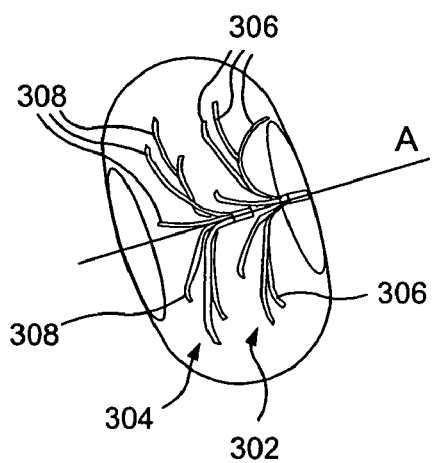
FIG. 11 is a diagram showing a heat generation zone for the bipolar system of FIG. 6 with electrode arrays thereof in a first position.

A method of use of the system 300 according to an exemplary embodiment of the present invention is described with reference to FIGS. 6 and 11-13. After the arrays 302, 304 have been positioned and deployed in position with the tines 306, 308 close to one another as shown in FIG. 11, RF energy is applied to the target tissue mass via the electrode arrays 302, 304. For example, this first energy application may be carried out with the linear portions 310, 312 of the tines 306, 308 separated from one another by a distance between approximately one quarter and one half of the diameter of the arrays 302, 304 to generate a lesion/high impedance area 305 in the target tissue having a large transverse size as compared to its length along the axis A. That is, the lesion initially generated will have a greater extent in a plane extending substantially perpendicular to an axis A of the system 300 than it has along the axis A.

Figure 12:
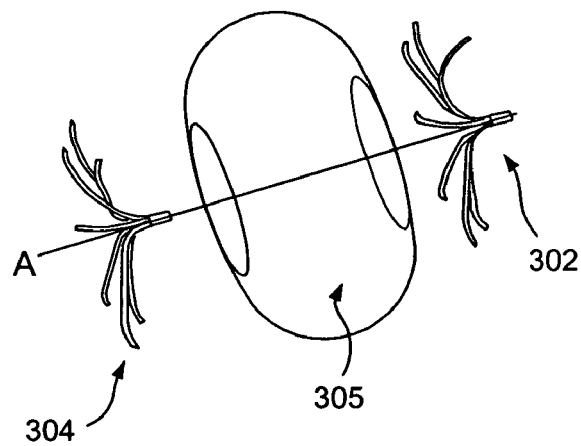
FIG. 12 is a diagram showing the electrode arrays of the bipolar system of FIG. 6 with the electrode arrays thereof in a second position after an initial ablation performed with the arrays in the first position.
Figure 13:
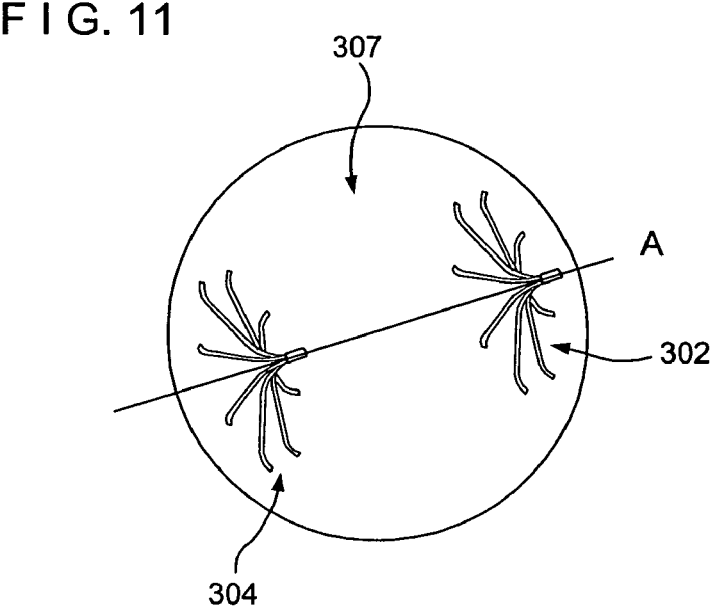
FIG. 13 is a diagram showing the bipolar system of FIG. 6 after ablation in the second position following an initial ablation performed with the arrays in the first position.

In a second step as shown in FIG. 12, the electrode arrays 302, 304 are repositioned further from one another near a transition region between the previously formed lesion/high impedance area 305 and the surrounding non-ablated tissue to further enlarge the lesion 305 along the axis A. The high impedance area 305 is now located between the electrode arrays 302, 304. Current then flows between the electrode arrays 302, 304 around the initial lesion/high impedance region 305 through initially unaffected tissue creating a substantially spherical combined lesion 307.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. An electrode assembly for a bi-polar ablation system comprising:
   a first electrode array including a plurality of first tines, each of the first tines, when in a deployed configuration, extending substantially radially away from a center of the first electrode array and including a straight central portion; and
   a second electrode array including a plurality of second tines, each of the second tines, when in the deployed configuration, extending substantially radially away from a center of the second electrode array and including a straight central portion parallel to the central portion of a corresponding one of the first tines, wherein each first tine and each second tine includes a further straight portion that extends from and forms a non-zero angle with the respective straight central portion.

2. The electrode assembly according to claim 1, wherein the first and second electrode arrays are mounted for movement relative to one another along an axis including the centers of the first and second electrode arrays.

3. The electrode assembly according to claim 1, wherein each of the first tines comprises a proximal portion coupled between a core of the first electrode array and the central portion and a distal portion extending from a distal end of the central portion, wherein the first electrode array core extends substantially parallel to a first axis of the first electrode array and wherein the proximal portions, when in the deployed configuration, curve away from proximal ends thereof substantially parallel to the core to distal ends extending radially away from the first axis.

4. The electrode assembly according to claim 1, wherein each of the second tines comprises a proximal portion coupled between a core of the second electrode array and the central portion and a distal portion extending from a distal end of the central portion, wherein the second electrode array core extends substantially parallel to a second axis of the second electrode array and wherein the proximal portions, when in the deployed configuration, curve away from proximal ends thereof substantially parallel to the core to distal ends extending radially away from the second axis.

5. The electrode assembly according to claim 1, wherein the first and second electrode arrays are moveable between the deployed configuration and an insertion configuration in which the first and second tines are folded substantially parallel to the first and second axes, respectively, to minimize outer diameters of the first and second arrays.

6. The electrode assembly according to claim 1, wherein the central portions of the first tines are adapted to cooperate with the central portions of the corresponding second tines to generate a substantially uniform current density distribution between at least those portions of the first and second electrode arrays adjacent to the central portions of the first and second tines.

7. The electrode assembly according to claim 1, wherein the central portion of each of the first and second tines comprises a majority of a length thereof.

8. The electrode assembly according to claim 1, wherein elements of the first electrode array do not contact elements of the second electrode array when a distance between the first and second electrode arrays is at least approximately one quarter of a diameter of the first and second electrode arrays when the first and second electrode arrays are in the deployed configuration.

9. A method for ablating tissue, comprising:
deploying a first electrode array at a first desired position relative to a target tissue mass to be ablated, the first electrode array comprising a plurality of first tines, each of the deployed first tines including a straight central portion;
deploying a second electrode array at a second desired position relative to the target tissue mass, the second electrode array comprising a plurality of second tines, each of the deployed second tines including a straight central portion, the central portions of the first and second tines being oriented and positioned so that a distance between corresponding pairs of the first and second tines is constant along the lengths thereof, the second desired position being separated from the first desired position by a distance between one quarter and one half of a deployed diameter of the first and second electrode arrays;
applying one of RF and electrical energy to the first and second electrode arrays to ablate a first portion of the target tissue mass;
repositioning at least one of the first and second electrode arrays to a third desired position relative to the target tissue mass to increase a distance between the first and second electrode arrays; and
applying one of RF and electrical energy the first and second electrode arrays to ablate a second portion of the target tissue mass.

10. The method according to claim 9, wherein the third desired position is adjacent a first portion of a transition region between the first portion of the target tissue mass and non-ablated tissue surrounding the first portion of the target tissue mass.

11. The method according to claim 10, further comprising repositioning the other of the first and second electrode arrays to a fourth desired position relative to the target tissue mass.

12. The method according to claim 11, wherein the fourth desired position is adjacent a second portion of the transition region between the first portion of the target tissue mass and non-ablated tissue surrounding the first portion of the target tissue mass.

13. A bi-polar ablation system comprising:
a cannula;
first and second electrode arrays mounted within the cannula for movement between an insertion configuration in which first tines of the first electrode array and second tines of the second electrode array are received within the cannula and a deployed configuration in which the first and second tines extend substantially radially outward from the cannula, each of the first and second tines, when in the deployed configuration, including a straight central portion, the central portion of each of the first tines being parallel to the central portion of a corresponding one of the second tines, wherein one of the first and second electrode arrays is moveable relative to the other along a length of the cannula; and
a source of one of RF and electrical energy coupleable to the first and second electrode arrays so that energy of opposite polarity is supplied to the first and second electrode arrays, respectively,
wherein each first tine and each second tine includes a further straight portion that extends from and forms a non-zero angle with the respective straight central portion of each first tine and each second tine.

14. The bi-polar ablation system assembly according to claim 13, wherein elements of the first electrode array do not contact elements of the second electrode array when a distance between the first and second electrode arrays is at least approximately one quarter of a diameter of the first and second electrode arrays when the first and second electrode arrays are in the deployed configuration.

* * * * *